United States Patent
Heide et al.

(10) Patent No.: US 10,345,127 B2
(45) Date of Patent: Jul. 9, 2019

(54) FLOWMETER AND CASSETTE MODULE FOR A FLOWMETER

(71) Applicant: FRESENIUS MEDICAL CARE DEUTSCHLAND GMBH, Bad Homburg (DE)

(72) Inventors: Alexander Heide, Eppstein (DE); Dejan Nikolic, Schwalbach am Taunus (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 120 days.

(21) Appl. No.: 15/548,886

(22) PCT Filed: Feb. 1, 2016

(86) PCT No.: PCT/EP2016/052040
§ 371 (c)(1),
(2) Date: Aug. 4, 2017

(87) PCT Pub. No.: WO2016/124527
PCT Pub. Date: Aug. 11, 2016

(65) Prior Publication Data
US 2018/0031399 A1 Feb. 1, 2018

(30) Foreign Application Priority Data
Feb. 4, 2015 (DE) .......... 10 2015 001 406

(51) Int. Cl.
*G01F 1/58* (2006.01)
*A61M 1/14* (2006.01)
(Continued)

(52) U.S. Cl.
CPC .......... *G01F 1/584* (2013.01); *A61M 1/1621* (2014.02); *A61M 1/1647* (2014.02); *G01F 1/58* (2013.01);
(Continued)

(58) Field of Classification Search
CPC ............ G01F 1/584; A61M 1/14; A61M 1/16
(Continued)

(56) References Cited

U.S. PATENT DOCUMENTS 3,002,379 A 10/1961 Hurley
4,351,189 A 9/1982 Gray et al.
(Continued)

FOREIGN PATENT DOCUMENTS

GB 2003274 3/1979
GB 2056691 3/1981
(Continued)

*Primary Examiner* — Jewel V Dowtin
(74) *Attorney, Agent, or Firm* — Jacobson Holman, PLLC.

(57) ABSTRACT

A cassette module for a differential flowmeter has a first channel and a second channel which carry fluid during operation of the differential flowmeter and are permeated by a magnetic field during operation of the differential flowmeter, each having an electrode pair arranged on the first channel and on the second channel. A flow difference between the first fluid-carrying channel and the second fluid-carrying channel can be determined by comparing the signals on the first electrode pair and on the second electrode pair. The first channel has an additional section that is permeated by the magnetic field during operation. Another electrode pair is arranged in the additional section, so that a change in the measurement conditions can be detected by comparing the signal on the first electrode pair and on the additional electrode pair.

15 Claims, 7 Drawing Sheets

(51) Int. Cl.
*A61M 1/16* (2006.01)
*G01F 15/14* (2006.01)
*G01F 25/00* (2006.01)

(52) U.S. Cl.
CPC ......... *G01F 15/14* (2013.01); *A61M 2205/12* (2013.01); *A61M 2205/3317* (2013.01); *A61M 2205/3334* (2013.01); *A61M 2205/70* (2013.01); *G01F 25/0007* (2013.01)

(58) Field of Classification Search
USPC .................................... 73/861.15; 210/321.6
See application file for complete search history.

(56) References Cited

U.S. PATENT DOCUMENTS

| | | |
|---|---|---|
| 4,585,552 A | 4/1986 | Gummesson et al. |
| 2013/0075314 A1* | 3/2013 | Nikolic .................. A61M 1/14 210/143 |

FOREIGN PATENT DOCUMENTS

| | | |
|---|---|---|
| WO | WO 00/19174 | 4/2000 |
| WO | WO 2011/113838 | 9/2011 |
| WO | WO 2013/164089 | 11/2013 |

\* cited by examiner

Fig. 1

PRIOR ART

FLOWMETER AND CASSETTE MODULE FOR A FLOWMETER

BACKGROUND OF THE INVENTION

1. Field of the Invention

The invention relates to a flowmeter, in particular a differential flowmeter for measuring a difference between a first fluid stream and a second fluid stream. The invention also relates to a cassette module having channels for the first and second fluid streams for use in a differential flowmeter.

2. Description of Related Art

Various methods are used for purification of blood and/or treatment of blood by machine to remove fluid and substances that must be removed in urine from patients with chronic renal failure. Diffusive mass transport is predominant in hemodialysis (HD), whereas hemofiltration (HF) is a convection mass transport through the membrane. Hemodiafiltration (HDF) is a combination of these two methods. In peritoneal dialysis (PD), no extracorporeal circulation is required and the peritoneum is used as a contact membrane.

Because of the large exchange volumes with the aforementioned methods as well as in continuous arterio-venous HF, continuous veno-venous HF and plasma filtration (PF), there is a need for accurate balancing of the fluid withdrawn, on the one hand, with the fluid supplied, on the other hand, and the quantity to be ultrafiltered over the total treatment time. Gravimetric and volumetric balancing systems are well-known in the prior art.

In addition, there are also known methods which continuously measure and balance the fluid streams of the fluids flowing into the dialyzer and the fluids flowing out of the dialyzer. Flowmeter sensors or flowmeters of various designs are used to do so.

Magnetic flowmeters, which are also known as electromagnetic flowmeters or inductive flowmeters, are based on measurement of the velocity of flow of a conductive fluid through a known or controlled magnetic field by measuring the induced electric voltage. In the case of a known flow cross section, it is possible to infer the flow rate or the volume flow from the velocity of flow, which should be covered by the concept of fluid flow in the following discussion. In a magnetic field through which the flow passes, an electrical voltage is generated by means of a charge separation of the ions, which are present in a conductive fluid and can be measured as an induced voltage. The voltage is typically measured by picking up the induced voltage on a pair of electrodes, which are in contact electrically with the conductive fluid, or which are coupled capacitively to the fluid. This voltage is proportional to the velocity of flow and depends on the magnetic field strength. The charge is separated in the direction perpendicular to the direction of flow and to the direction of the magnetic field. The magnetic field of a magnetic flowmeter is therefore preferably arranged at a right angle to the direction of flow in the corresponding fluid channel, and the electrode pair for picking up the induced electrical voltage is preferably arranged at a right angle to the magnetic field and also to the direction of flow in the fluid channel.

A typical electromagnetic flowmeter is constructed from a nonmagnetic and nonmagnetizable tube which is lined on the inside with electrically insulating material.

The magnetic field is typically generated by one or more coils arranged outside of the tube, through which the fluid flows. The electrical voltage induced by the fluid flow is typically determined by a voltmeter, and the result of the voltage measurement is sent to an evaluation unit for determination of the fluid stream, i.e., the flow rate or the volume flow, based on the measured voltage.

If an electromagnetic flowmeter is designed as a differential flowmeter for measuring a flow difference between a first and a second fluid-carrying channel, then a common magnetic field advantageously penetrates through the first and second fluid-carrying channels.

If the first and second fluid-carrying channels match one another with regard to their geometric dimensions, then the voltage difference between a first electrode pair arranged on the first fluid-carrying channel and a second electrode pair arranged on the second fluid-carrying channel will indicate directly the difference between the flow in the first channel and the flow in the second channel. This voltage difference can be picked up directly if the first and second electrode pairs are connected in series.

An electromagnetic differential flowmeter is advantageously formed from the one cassette module, in which the fluid-carrying channels are designed, each of which has an electrode pair, an electromagnet or permanent magnet for generating a magnetic field between the electrode pair and an evaluation unit and for evaluating the voltages or the differential voltage between the electrode pairs.

Differential flowmeters according to the electromagnetic principle have a high sensitivity to a change in position (with respect to the magnetic field) of the fluid-carrying channels.

The object of the present invention is therefore to make available an improved differential flowmeter.

SUMMARY OF THE INVENTION

This object is achieved by a cassette module as described herein, as well as by a differential flowmeter as described herein. Advantageous refinements of the invention are also described herein.

In accordance with the teaching of the present invention, a cassette module for a differential flowmeter is made available. A first channel and a second channel are formed in the cassette module; during operation of the differential flowmeter, these channels carry fluid and each one is permeated by a magnetic field during operation of the differential flowmeter. One electrode pair, i.e., a first electrode pair on the first channel and a second electrode pair on the second channel, is arranged on the first and second channels, respectively. By comparing the signal on the first electrode pair and the second electrode pair, a flow difference between the first and second fluid-carrying channels can be determined, approximately the difference between the volume flow, between the fluid flowing in the first channel and the fluid flowing in the second channel, based on a difference in the flow rate in the first channel and the second channel and knowledge of the respective channel geometry. The first fluid-carrying channel during operation has a first section, in which the fluid flows in a predetermined direction and has another section, preferably a return section, i.e., a section in which the fluid flows essentially in a direction opposite the predetermined direction. Another electrode pair is arranged on the return section. A change in the measurement conditions can be detected by comparing the signal on the first electrode pair with that on the second electrode pair.

In an advantageous embodiment of the cassette module, the second fluid-carrying channel during operation has an additional section, which is penetrated by the magnetic field during operation, preferably a return section, i.e., the second channel forms a first section and the return channel, wherein the direction of flow in the first section and additional section points essentially in an opposite direction. A fourth electrode pair is arranged on the second section. A change in the measurement conditions can thus be detected by comparing the voltage on the second electrode pair and the voltage on the fourth electrode pair.

An additional possibility for checking the measurement conditions is provided in this way.

In accordance with the teaching of the present invention, a differential flowmeter is supplied with a cassette module, as described above. The differential flowmeter has an evaluation unit connected to the first, second and additional electrode pairs. The evaluation unit is configured so that a flow difference between the first and the second fluid-carrying channels can be determined by comparing the signal on the first and second electrode pairs, and it is further configured so that a change in the measurement conditions can be detected by comparing the signal on the first electrode pair and the additional electrode pair. In one embodiment, the differential flowmeter has a permanent magnet or an electromagnet for generating the magnetic field.

In a refinement of the differential flowmeter, the evaluation unit is configured so that a change in the position of the cassette module in the magnetic field can be detected by comparing the signal on the first electrode pair and additional electrode pairs.

In other words, a change in the measurement conditions is interpreted as meaning that it can be traced back to a change in position of the cassette module in the magnetic field.

In an advantageous refinement of the differential flowmeter, the evaluation unit is configured so that a change in the measurement conditions can be detected by comparing the signal on the second and fourth electrode pairs.

An additional possibility for checking the measurement conditions is provided in this way.

In one embodiment of the differential flowmeter, the evaluation unit is configured so that a change in the position of the cassette module in the magnetic field can be detected by comparing the signal on the second electrode pair and that on the fourth electrode pair.

A change in the measurement conditions is thus interpreted as meaning that it is attributed to a change in position of the cassette module in the magnetic field.

In one advantageous embodiment of the differential flowmeter, the second fluid-carrying channel has a first section and the return section, and the first section and the return section are arranged side by side with respect to the direction of the magnetic field.

Thus, in the event of an inhomogeneity in the magnetic field, a change in the position of the cassette module can be detected with a high sensitivity.

In an advantageous refinement of the differential flowmeter, the first and second fluid-carrying channels are arranged one after the other with respect to the direction of the magnetic field.

In this way, a differential flowmeter may be designed so that there is only a slight sensitivity to changes in position of the cassette module in the magnetic field.

In another advantageous refinement of the differential flowmeter, the first fluid-carrying channel has a first section and the return section, and the first section and the return section are arranged side by side with respect to the direction of the magnetic field.

In this way, when there is an inhomogeneity in the magnetic field, a change in the position of the cassette module can be detected with a great sensitivity.

In one advantageous refinement of the differential flowmeter, the evaluation unit is adjusted to initiate and/or perform a recalibration as a response to a finding of the change in the measurement conditions.

The measurement accuracy can be restored by a recalibration in this way.

In another embodiment of the differential flowmeter, a short-circuit line and a shut-off device are provided for short-circuiting the first and second channel and the shut-off device is controllable in such a way that the first and second channels are short-circuited in recalibration.

DETAILED DESCRIPTION OF THE PREFERRED EMBODIMENTS

Further scope of applicability of the present invention will become apparent from the detailed description given hereafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
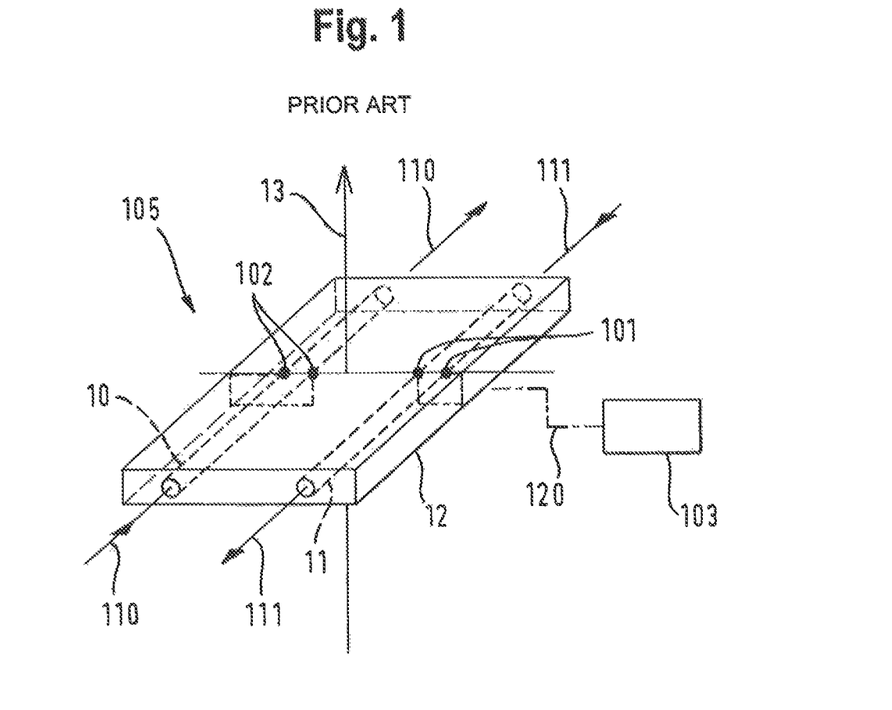
FIG. 1 shows a typical design of a differential flowmeter having a cassette module (prior art).

FIG. 1 shows the typical design of an electromagnetic differential flowmeter 105 for determining a fluid balance. The differential flowmeter 105 has a cassette module 12, in which the fluid-carrying channels 10 and 11 are designed and between which fluid is to be balanced. During use of the differential flowmeter, the fluid-carrying channels 10 and 11 are typically connected to a fluid circulation, in which a fluid balance is to be determined, for example, in the dialysis fluid circulation of a dialysis machine.

The cassette module 12 is permeated by a magnetic field 13, indicated by the magnetic field line, the magnetic field being generated by an electric magnet or a permanent magnet (not shown).

The first fluid-carrying channel 10 has fluid flowing through it in the direction of flow 110 indicated in the opposite direction of the direction of flow 111 in the second fluid-carrying channel 11.

The ions present in the fluid in the channels 10 and 11 are subject to charge separation due to the flow perpendicular to the magnetic field 13, and this charge separation can be picked up as a potential difference on the first electrode pair 102 and the second electrode pair 101, which are each arranged on the fluid-carrying channels.

The first electrode pair 102 and the second electrode pair 101 are connected to the evaluation unit 103 by means of measurement lines 120.

A fluid balance or a differential flow between the first fluid-carrying channel 10 and the second fluid-carrying channel 11 is determined in the evaluation unit 103, for example, as the difference between the volume flows in the first fluid-carrying channel 10 and in the second fluid-carrying channel 11 by comparing the voltage picked up on the first electrode pair 102 and the voltage picked up on the second electrode pair 101.

Figure 2A:
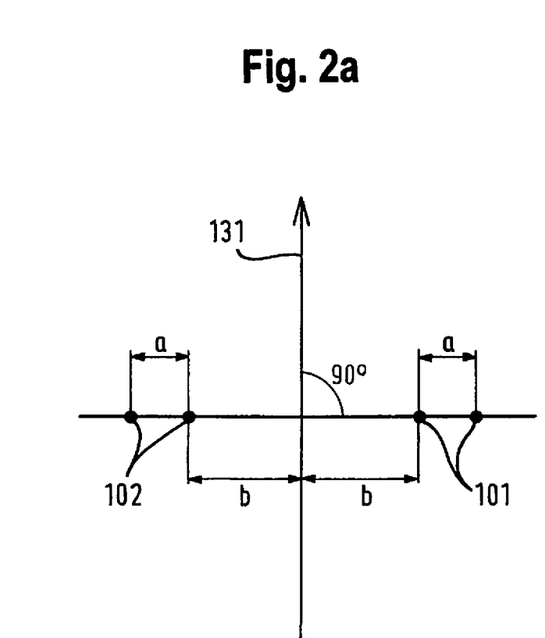
FIG. 2a shows the geometric position relationships in the cassette module shown in FIG. 1 in an ideal position.

FIG. 2a shows the arrangement of the electrode pairs 102, 101 in the magnetic field and the geometric dimensions in the differential flowmeter shown in FIG. 1 in an ideal position. A direction arrow indicates the direction 131 of the magnetic field in the differential flowmeter as well as a line of symmetry of the magnetic field. The electrode pairs 102 and 101 sit on an imaginary line perpendicular to the direction 131 of the magnetic field, where "a" denotes the—matching—distance between the electrodes of the first electrode pair 102 and those of the second electrode pair 101; "b" refers to the—matching—distance between the electrode of the respective electrode pair 102, 101 facing the center and the imaginary center line between the electrode pairs. The configuration shown in FIG. 2a is an ideal configuration in the sense that the distances "a" between the electrodes of the electrode pairs 102, 101 both match, and the electrode pairs 102, 101 are each the same distance "b" from the line of symmetry of the magnetic field. It is thus possible to infer the difference in flow between the flow in the first channel and the flow in the second channel, for example, a difference between the volume flow in the first channel and the volume flow in the second channel by comparing the voltage picked up on the first electrode pair 102 and the voltage picked up on the second electrode pair 101, for example, by forming a difference between the voltage picked up on the first and second electrode pairs. Thus, with the ideal configuration shown in FIG. 2a, a voltage difference zero between the voltage on the first electrode pair 102 and the voltage on the second electrode pair 101 corresponds to a flow difference of zero. A relationship between the voltages picked up on the electrode pairs 102, 101 and the respective volume flows can be established with the help of calibration measurements and the result is stored in the evaluation unit 103.

Figure 2B:
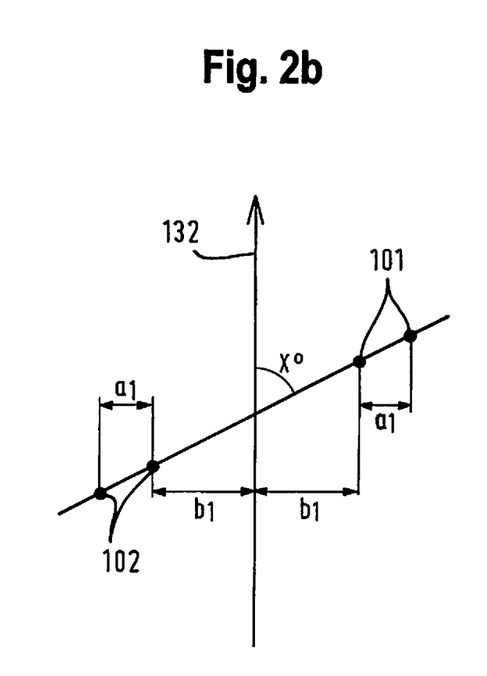
FIG. 2b shows the geometric position relationships in the cassette module shown in FIG. 1 in a position which differs from the ideal position.

FIG. 2b shows the arrangement of the electrode pairs 102, 101 in the magnetic field as well as the geometric dimensions in the differential flowmeter shown in FIG. 1 in a position different from the ideal position. A directional arrow indicates the direction 132 of the magnetic field in the differential flowmeter, this direction differing from the line of symmetry of the magnetic field. The electrode pairs 102 and 101 lie on an imaginary line at an angle of x° to the direction 132 of the magnetic field, where "a1" denotes the—matching—projection of the distance of the electrodes of the first electrode pair 102 and of the second electrode pair 101 onto a line perpendicular to the direction 132 of the magnetic field, and "b1" denotes the—matching—projection of the distance of the electrode of the respective electrode pair 102, 101 facing the center, onto a line perpendicular to the direction of the magnetic field. The configuration shown in FIG. 2b differs from the ideal configuration in the sense that the projection of the distance "a1" differs from the distance in FIG. 2a, with the distance designated as "a" in FIG. 2a between the electrodes of the electrode pairs 102, 101, and that the projections "b1" of the distance of the electrode pairs 102, 101 differ from the distance labeled as "b" in FIG. 2a. The change in the distance from "a" to "a1" leads to a change in the voltages dropped on the electrode pairs 102, 101 with otherwise identical flows and identical size of the magnetic field. If the magnetic field has inhomogeneities, then a change in the distance from "b" to "b1" leads to a significant change in the magnetic field at the site of the first electrode pair 102 and at the site of the second electrode pair 101. Thus, there is a change in the voltages picked up on the first electrode pair 102 and on the second electrode pair 101, with no change in the volume flows, and with the measurement results based on the voltages picked up.

Figure 2C:
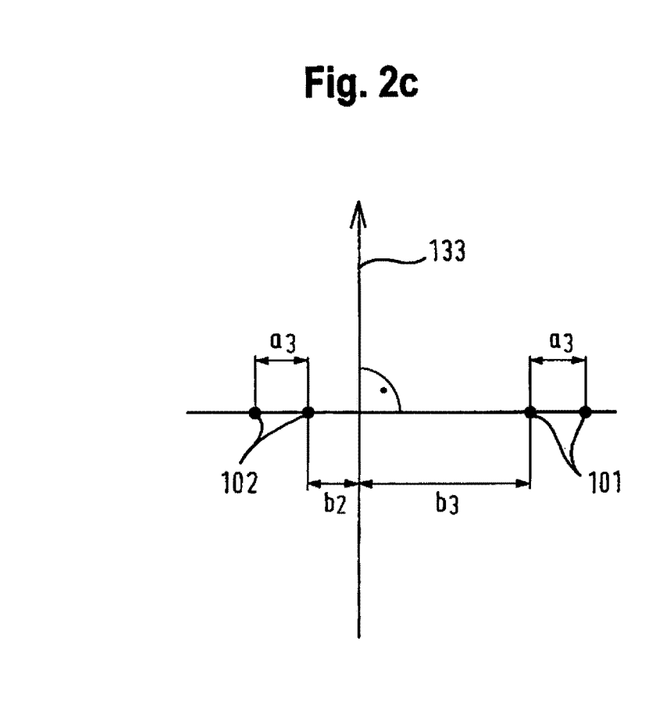
FIG. 2c shows the geometric position relationships in the cassette module shown in FIG. 1 in another position which differs from the ideal position.

FIG. 2c shows the arrangement of the electrode pairs 102, 101 in the magnetic field as well as the geometric dimensions in the differential flowmeter shown in FIG. 1 in another position, different from the ideal position. A directional arrow indicates the direction 133 of the magnetic field in the differential flowmeter as well as a line of symmetry of the magnetic field. The electrode pairs 102 and 101 lie on an imaginary line perpendicular to the direction 133 of the magnetic field, where "a3" denotes the—matching—distance of the electrodes of the first electrode pair 102 and of the second electrode pair 101 and "b2" and "b3" each denote the different distances of the electrodes of the respective electrode pair 102, 101 facing the center from the imaginary center line between the electrode pairs. The configuration shown in FIG. 2c differs to this extent from the ideal configuration since the electrode pairs 102 and 101 are not arranged symmetrically in the magnetic field. If the magnetic field has inhomogeneities or an asymmetry, then the voltages picked up on the first electrode pair 102 and the second electrode pair 101 change when conditions are otherwise unchanged, for example, unchanged fluid flows.

Figure 2D:
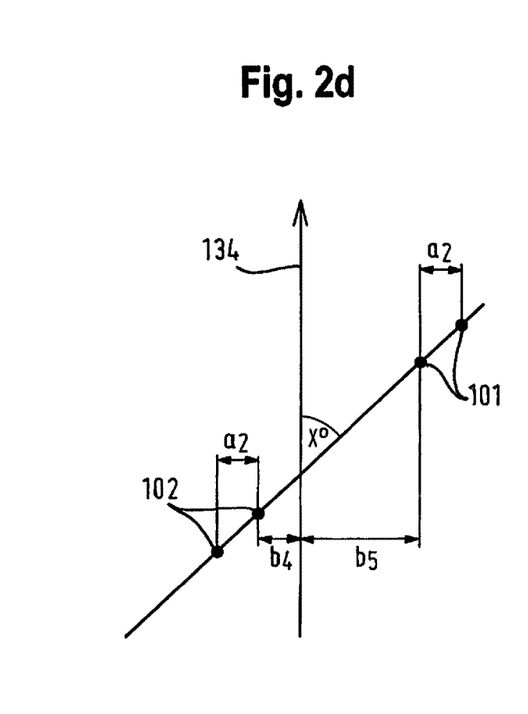
FIG. 2d shows the geometric position relationships in the cassette module shown in FIG. 1 in a third position which differs from the ideal position.

FIG. 2d shows the arrangement of the electrode pairs 102, 101 in the magnetic field as well as the geometric dimensions in the differential flowmeter shown in FIG. 1 in a third position which differs from the ideal position. A directional arrow indicates the direction 134 of the magnetic field in the differential flowmeter which differs from the line of symmetry of the magnetic field. The electrode pairs 102 and 101 lie on an imaginary line at an angle x° to the direction 134 of the magnetic field where "a2" denotes the—matching—projection of the distance of the electrodes of the first electrode pair 102 and of the second electrode pair 101 onto a line perpendicular to the direction 134 of the magnetic field and "b4" and "b5" each denote different projections of the distance of the electrodes of the respective electrode pair 102, 101 facing the center of the respective pair to a line perpendicular to the direction of the magnetic field. The configuration shown in FIG. 2d differs from the ideal configuration in the sense that the projection of the distance "a" in comparison with the distance in FIG. 2a differs from the distance labeled as "a" in FIG. 2a between the electrodes of the electrode pairs 102, 101, and the electrode pairs 102, 101 are not arranged symmetrically in the magnetic field. This leads to a change in the voltages dropping on the electrode pairs 102, 101 as well as to voltages of different sizes on the electrode pairs 102 and 101 when the volume flows in the first channel and in the second channel are the same—based on the diagrams in FIG. 1.

Figure 3A:
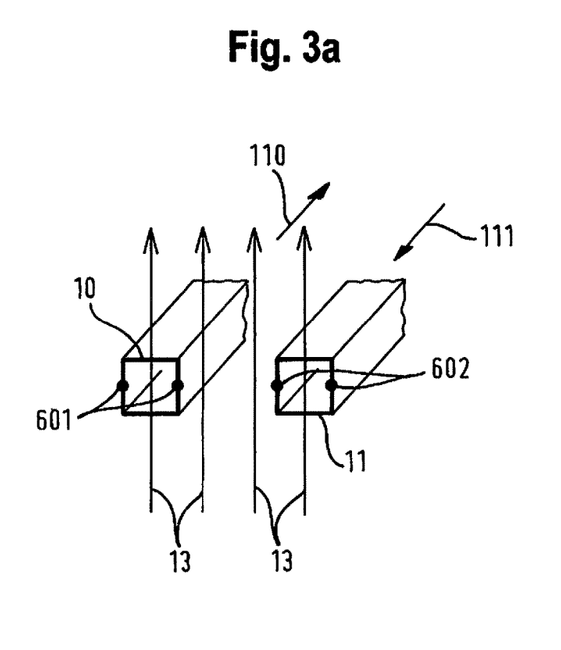
FIG. 3a shows an arrangement of fluid-carrying channels of a cassette module in a magnetic field.

FIG. 3a shows a three-dimensional diagram of an arrangement of fluid-carrying channels 11, 10 of a cassette module in an electromagnetic differential flowmeter. The differential flowmeter corresponds in its function essentially to the differential flowmeter described in relation to FIG. 1, to which reference is herewith made instead of repeating it. The arrangement of the fluid-carrying channels 11, 10 with respect to the direction of the magnetic field corresponds to the arrangement shown in FIG. 1, i.e., the first fluid-carrying channel 10 and the second fluid-carrying channel 11 are arranged side by side with respect to the direction of the magnetic field. The first fluid-carrying channel 10 has the fluid flowing therein in a direction of flow 110, which is essentially opposite the direction of flow 111 in the second fluid-carrying channel 11. The electrode pairs 601, 602 are arranged on the first fluid-carrying channel 10 and on the second fluid-carrying channel 11. With regard to the position of the electrodes relative to the magnetic field 13 and to the direction of flow 110, 111 in the channels, this corresponds essentially to the situation illustrated in FIG. 1.

Figure 3B:
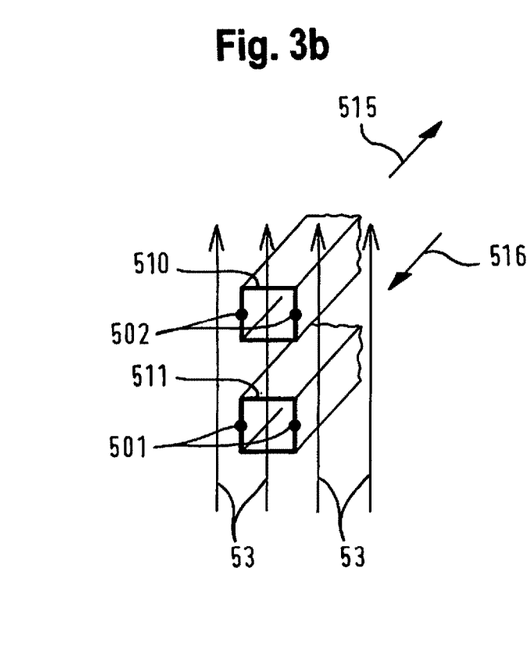
FIG. 3b shows another arrangement of fluid-carrying channels of a cassette module in a magnetic field.

FIG. 3b shows a three-dimensional diagram of an arrangement of fluid-carrying channels 511, 510 of a cassette module with respect to a magnetic field 53 in an electromagnetic differential flowmeter. With regard to the function, the differential flowmeter corresponds essentially to the differential flowmeter described in relation to FIG. 1, to which reference is herewith made instead of repeating it. The arrangement of the fluid-carrying channels 511, 510 shown in FIG. 3b with respect to the direction of the magnetic field 53 differs from the arrangement of FIGS. 1 and 3a, i.e., the first fluid-carrying channel 510 and the second fluid-carrying channel 511 are arranged one after the other with respect to the direction of the magnetic field. With this arrangement, there is only a low sensitivity of the differential flow sensor when the position of the fluid-carrying channels 510, 511 in the magnetic field changes. The first fluid-carrying channel 510 has fluid flowing through it in a direction of flow 515 essentially opposite the direction of flow 516 in the second fluid-carrying channel 511. Electrode pairs 501, 502 are arranged on the first fluid-carrying channel 510 and on the second fluid-carrying channel 511, and the connecting lines between the electrodes of the electrode pairs 501, 502 are each arranged essentially perpendicular to the direction of the magnetic field 53 and to the direction of flow 515 and to the direction of flow 516.

Figure 4A:
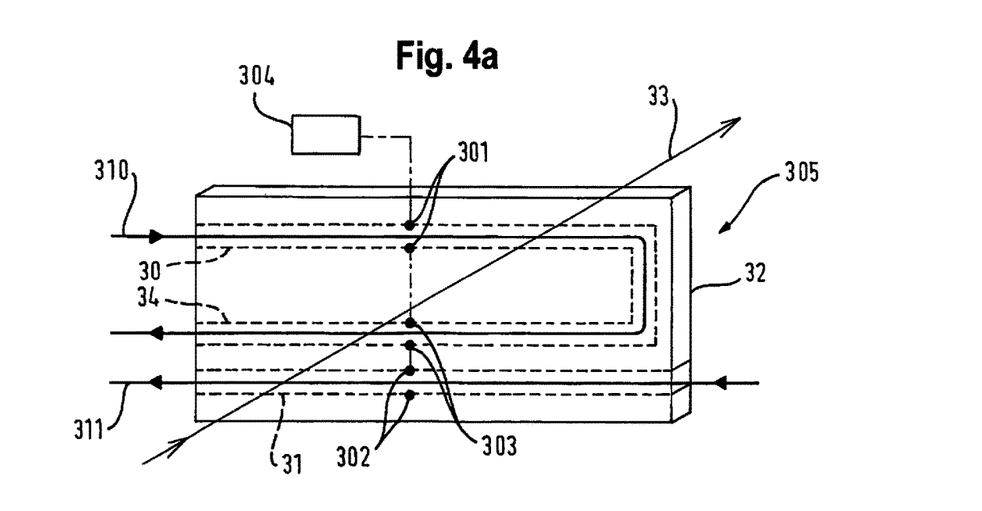
FIG. 4a shows one embodiment of a differential flowmeter in accordance with the present teaching.

FIG. 4a shows the design of an electromagnetic differential flowmeter 305 for determining a fluid balance, in one exemplary embodiment in agreement with the teaching of the present invention. The differential flowmeter 305 has a cassette module 32 in which a first fluid-carrying channel 30 and a second fluid-carrying channel 31 are provided, with the fluid to be balanced between them. The first fluid-carrying channel has a first section and a return section 34, i.e., the fluid to be balanced flows in a predetermined direction in the first section and the fluid in the return section flows essentially in a direction opposite the predetermined direction.

The fluid-carrying channels 30 and 31 are typically connected to a fluid circulation in which a fluid balance is to be determined, for example, in the dialysis fluid circulation of a dialysis machine during use of the differential flowmeter.

The cassette module 32 is penetrated by a magnetic field 13, which is indicated by the magnetic field line and is generated by an electric magnet or a permanent magnet (not shown).

The direction of flow in the first and return section 34 is perpendicular to the direction of the magnetic field 33.

In a first section, the first fluid-carrying channel 30 has a flow passing through it in the direction of flow 310 indicated, flowing opposite the direction of flow 311 in the second fluid-carrying channel 31.

The ions present in the fluid in the first channel 30 are subject to charge separation due to the flow perpendicular to the magnetic field 33. This can be picked up as a potential difference from the first electrode pair 301 and additional electrode pair 303 arranged on the first section and the return section of the first channel.

The charge separation of the ions present in the second channel 31 may be picked up as a potential difference on a second electrode pair 302.

The first electrode pair 301, the second electrode pair 302 and the additional electrode pair 303 are connected by measurement lines 320 to the evaluation unit 304.

The evaluation unit is configured to determine a fluid balance between the volume flow in the first fluid-carrying channel 30 and in the second fluid-carrying channel 31 and on the other hand, to detect a change in the measurement conditions, in particular a change in position of the cassette module 32 in the magnetic field 33.

By comparing the voltage picked up on the first electrode 301 and the voltage picked up on the second electrode pair 302, a fluid balance or a differential flow between the first fluid-carrying channel 30 and the second fluid-carrying channel 31 can be determined in the evaluation unit 304, for example, as the difference between the volume flow in the first fluid-carrying channel 30 and the volume flow in the second fluid-carrying channel 31.

If equal volume flows can prevail in first fluid-carrying channel 30 and in the second fluid-carrying channel 31 by controlling a calibration device, then a zero point of the fluid balance can be determined by comparing the voltage picked up on the first electrode pair 301 with the voltage picked up on the second electrode pair 302. A corresponding calibration device is described in relation to FIGS. 6a and 6b.

By comparing the voltage picked up on the first electrode pair 301 and the voltage picked up on the additional electrode pair 303, a change in the measurement conditions can be determined in the evaluation unit 304, in particular a change in position of the cassette module 32 in the magnetic field.

If a change in the measurement conditions is detected, then a calibration is advantageously initiated and performed as described above.

Figure 4B:
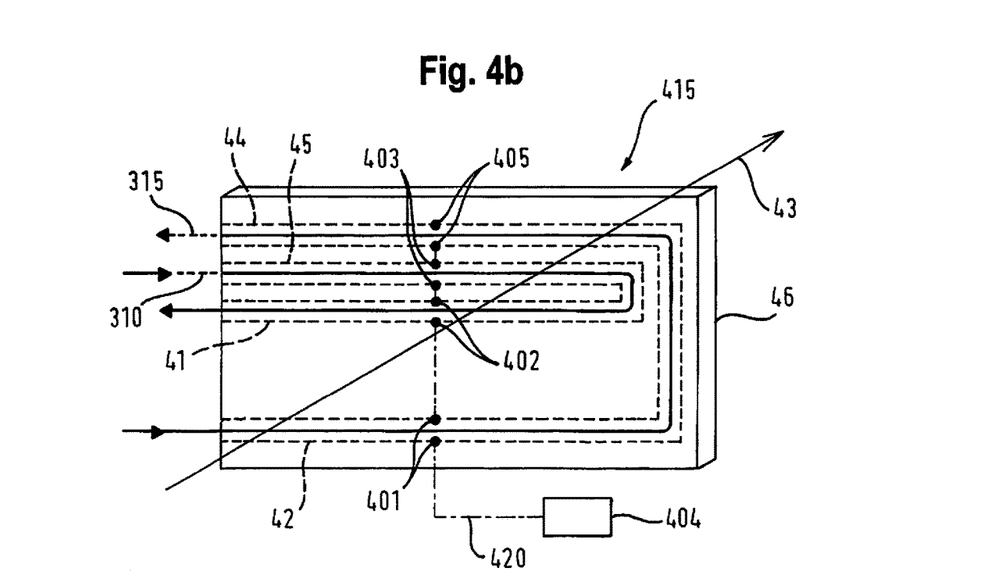
FIG. 4b shows another embodiment of a differential flowmeter in accordance with the present teaching.

FIG. 4b shows the design of an electromagnetic differential flowmeter 415 for determining a fluid balance in an additional exemplary embodiment which is consistent with the teaching of the present invention. The differential flowmeter 415 has a cassette module 46 in which a first channel 45 which fluid carrying during operation and a second channel 44 which is fluid carrying during operation are formed and between which a fluid balance is to be determined. The first fluid-carrying channel 45 and the second fluid-carrying channel 44 each have a first section and a return section, i.e., the first channel 45 has a return section 41 and the second channel 44 has a return section 42. In the first section, the fluid to be balanced flows in the first channel and also in the second channel 44, each in a certain direction, and in the return section, the fluid flows essentially in a direction opposite this direction.

The fluid-carrying channels 45 and 44 are typically connected to a fluid circulation during use of the differential flowmeter, such that a fluid balance is to be determined in this fluid circulation, for example, in the dialysis fluid circulation of a dialysis machine.

The magnetic field 43 permeating the cassette module 46 is generated by an electromagnet or a permanent magnet (not shown).

For the first channel 45 and the second channel 44, the direction of flow in the first section 41 and in the second section 42 is essentially perpendicular to the direction of the magnetic field.

In the first section 41, the first fluid-carrying channel 45 has flow passing through it in the direction of flow 310 indicated, which is opposite the direction of flow 315 in the first section of the second fluid-carrying channel 44.

The ions present in the fluid in the first channel 45 are subject to charge separation due to the flow perpendicular to the magnetic field 43. This charge may be picked up as a potential difference on the first electrode pair 403 and the additional electrode pair 402, each arranged on the first section and the return section of the first channel.

Likewise, the flow in the second channel 44 leads to a charge separation, which can be picked up as a potential difference on the second electrode pair 405 and the fourth electrode pair 401, which are arranged on the first section and the return section 42 of the second channel.

The first electrode pair 403, the second electrode pair 405, the additional electrode pair 402 and the fourth electrode pair 401 are connected to the evaluation unit 404 by measurement lines 420.

The evaluation unit 440 is configured to determine, on the one hand, a fluid balance between the volume flow in the first fluid-carrying channel 45 and in the second fluid-carrying channel 44 and, on the other hand, to detect a change in the measurement conditions, in particular a change in the position of the cassette module 46 in the magnetic field 43.

The fluid balance or the differential flow between the first fluid-carrying channel 45 and the second fluid-carrying channel 44 is determined in the evaluation unit 404 on the basis of a comparison of the voltage picked up on the first electrode pair 403 and the voltage picked up on the second electrode pair 405.

The fluid difference between the first and second fluid-carrying channels may be expressed as the difference between the volume flow in the first fluid-carrying channel 45 and that in the second fluid-carrying channel 44.

If, by controlling a calibration device, the same volume flows can prevail in the first channel 45 and in the second fluid-carrying channel 44, then by comparing the voltage picked up on the first electrode pair 403 with the voltage picked up on the second electrode pair 405, a zero point of the fluid balance can be determined and saved as a calibration value. A corresponding calibration device is described in relation to FIGS. 6a and 6b.

The change in the measurement conditions or the change in position is determined by comparing the voltages on the electrode pairs arranged on the same channel, i.e., by comparing the voltage picked up on the first electrode pair 403 and the voltage picked up on the additional electrode pair 402 and/or by comparing the voltage picked up on the second electrode pair 405 and on the fourth electrode pair 401.

If a change in the measurement conditions is detected, then a calibration is advantageously initiated and carried out as described above.

Figure 5:
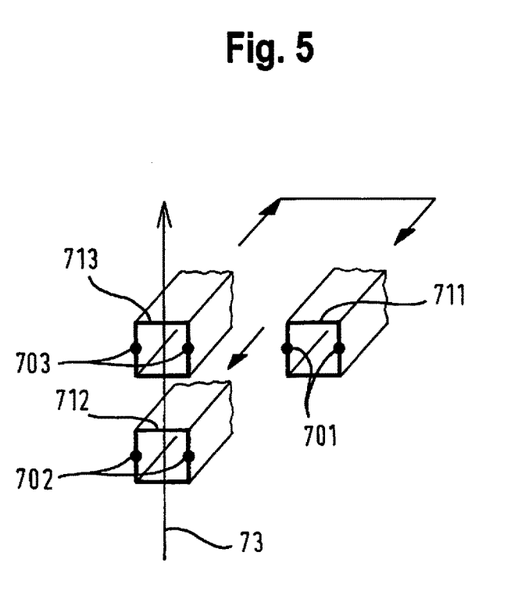
FIG. 5 shows an arrangement of fluid-carrying channels of a cassette module in the magnetic field in accordance with the present teaching.

FIG. 5 shows a three-dimensional diagram of an arrangement of fluid-carrying channels 712 and their sections 713, 711 of a cassette module with respect to a magnetic field 73 in an electromagnetic differential flowmeter. With regard to function, the differential flowmeter corresponds essentially to the differential flowmeter described in relation to FIG. 4a; reference is made to this description instead of repeating it here. This shows the first section 713 of the first channel, the return section 711 of the first channel and the second channel 712, each of which is designed in the cassette module. The arrangement of the channels, which are fluid-carrying during operation, and/or their sections 713, 712 and 711 with respect to the direction of the magnetic field 73 differs from the arrangement in FIG. 4a. In the embodiment in FIG. 5, the first section 713 of the first channel and the second channel 712 are arranged one after the other with respect to the direction of the magnetic field. With this arrangement the differential flow sensor has a low sensitivity when the positions of the fluid-carrying channels 712, 713, 711 in the magnetic field change. On the other hand, the first section 713 and the return section 711 of the first channel are arranged side by side with respect to the direction of the magnetic field 73. If there is inhomogeneity or asymmetry in the magnetic field, the change in the position of the cassette module in the magnetic field can be detected with a high sensitivity.

The first section 713 of the first fluid-carrying channel has flow passing through it in a direction of flow that is essentially opposite the direction of flow in the second fluid-carrying channel 711.

Likewise the first section 713 and the return section 711 of the first channel have fluid flowing through them essentially in the opposition direction of flow.

Electrode pairs 703, 701 are arranged on the first section 713 and on the second section 711 of the first fluid-carrying channel, and one electrode pair 702 is arranged on the second fluid-carrying channel. The connecting lines between the electrodes of the electrode pairs 701, 702, 703 are each arranged essentially perpendicular to the direction of the magnetic field 73 and to the flow in the fluid-carrying channels.

Figure 6A:
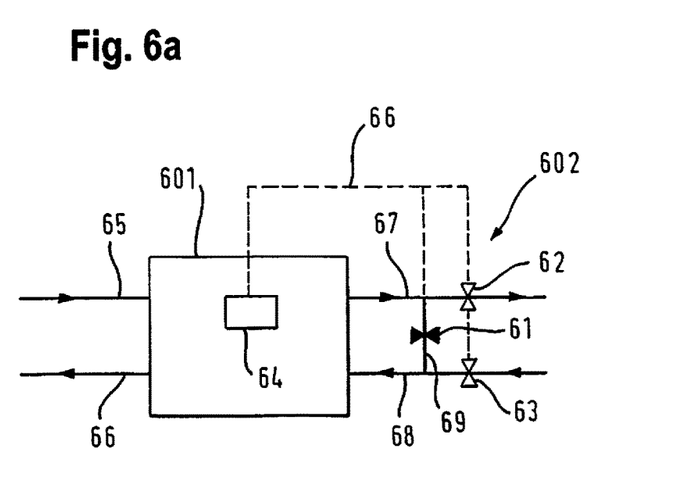
FIG. 6a shows an embodiment of a differential flowmeter with a calibration unit in a first operating mode.

FIG. 6a shows an embodiment of a differential flowmeter 601 with a calibration unit 602. The differential flowmeter 601 is advantageously designed according to the differential flowmeter 305 described in relation to FIG. 4a or according to the differential flowmeter 415 described in relation to FIG. 4b. The differential flowmeter 601 has an evaluation and control unit 64, which carries out the functions of the evaluation unit 304, described in relation to FIG. 4a with regard to its function as an evaluation unit and/or the functions of the evaluation unit 404, described in relation to FIG. 4b.

This also shows an inflow 65 to the first channel of the differential flowmeter 601 and an outflow 67 from the first channel of the differential flowmeter as well as an inflow 68 from the second channel and an outflow 66 from the second channel.

Between the outflow 67 and the inflow 68, there is a short-circuit line 69 with a shut-off device 61. In addition shut-off devices 62 and 63 are arranged in the outflow 67 and in the inflow 68.

The control unit 64 is connected to the shut-off devices 61, 62, 63 via control lines 66.

Fundamentally, two modes of operation are provided for the differential flowmeter 601: a "balancing" mode of operation and a "calibration" mode of operation. In the "balancing" mode of operation, the shut-off device 61 of the short-circuit line 69 is closed or kept closed and the differential flowmeter determines a fluid balance as described above in relation to the differential flowmeter 305 of FIG. 4a or the differential flowmeter 415 of FIG. 4b. The closed position of the shut-off device 61 in the "balancing" mode of operation is represented in FIG. 6a by the thoroughly solid-colored representation of the shut-off device 61.

In the "balancing" mode of operation, the shut-off devices 62 and 63 are opened or kept open, which is indicated in FIG. 6a by the transparent representation of the shut-off devices 62 and 63.

In the "calibration" mode of operation, the differential flowmeter is calibrated, in particular the evaluation and control unit 64.

The invention being thus described, it will be apparent that the same may be varied in many ways. Such variations are not to be regarded as a departure from the spirit and scope of the invention, and all such modifications as would be recognized by one skilled in the art are included within the scope of the following claims.

Calibration of the evaluation and control unit serves to determine the zero point of the fluid balance, i.e., an operating point at which the liquid flow in the first channel and the fluid flow in the second channel correspond, as described above in relation to FIG. 4a and FIG. 4b.

Figure 6B:
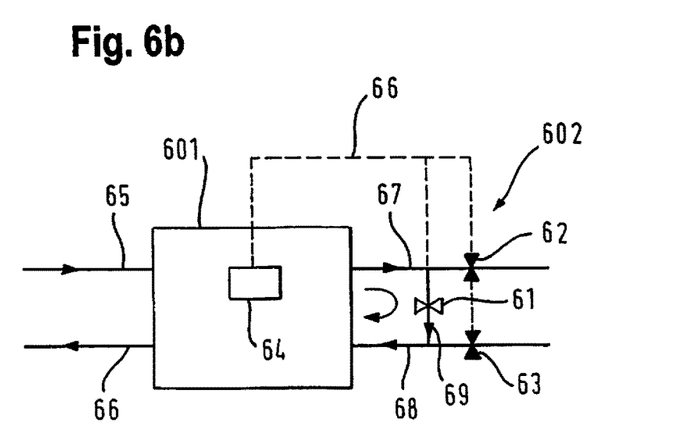
FIG. 6b shows an embodiment of a differential flowmeter with a calibration unit in another operating mode.

In the "calibration" mode of operation, the evaluation and control unit controls the shut-off devices 61, 62, 63 so that a short circuit between the outflow 67 and the inflow 68 and thus a short circuit between the first and the second channels is established. To do so, the shut-off device 61 in the short-circuit line 69 is opened or kept open and the shut-off devices 62 and 63 are closed or kept closed.

The open position of the shut-off device 61 in the short-circuit line 69 is indicated in FIG. 6b by the transparent representation of the shut-off device 61. The closed position of the shut-off devices 62, 63 is represented by the solid colored position.

What is claimed is:

1. A cassette module for a differential flowmeter, the cassette module comprising:
   a first channel and a second channel which carry a fluid during operation of the differential flowmeter, and which are permeated by a magnetic field during operation of the differential flowmeter, each having an electrode pair arranged on the first fluid-carrying channel and on the second fluid-carrying channel, so that a flow difference between the first fluid-carrying channel and the second fluid-carrying channel can be determined by comparing signals on a first electrode pair and on a second electrode pair,
   the first fluid-carrying channel including a first channel additional section that is permeated by the magnetic field during operation, and an additional electrode pair arranged in the first channel additional section so that a change in measurement conditions can be detected by comparing the signal on the first electrode pair and on the additional electrode pair.

2. The cassette module for a differential flowmeter according to claim 1, wherein the second fluid-carrying channel includes a second channel additional section, which is permeated by the magnetic field during operation, and a fourth electrode pair is arranged in the second channel additional section, so that, by comparing the voltage on the second electrode pair and on the fourth electrode pair, a change in the measurement conditions can be detected.

3. The cassette module for a different flowmeter according to claim 1, further comprising an evaluation unit connected to the first electrode pair and the second electrode pair and the additional electrode pair,
   wherein the evaluation unit is configured so that, by comparing the signal on the first electrode pair and on the second electrode pair, a flow difference can be determined between the first fluid-carrying channel and the second fluid-carrying channel and
   wherein the evaluation unit is also configured so that a change in the measurement conditions can be detected by comparing the signal on the first electrode pair and on the additional electrode pair.

4. The cassette module for a differential flowmeter according to claim 3, wherein the evaluation unit is configured so that a change a position of the cassette module in the magnetic field can be detected by comparing the signal on the first electrode pair and on the additional electrode pair.

5. The cassette module for a differential flowmeter according to claim 3, wherein the second fluid-carrying channel includes a second channel additional section, which is permeated by the magnetic field during operation, and a fourth electrode pair arranged in the second channel additional section,
   wherein the evaluation unit is configured so that a change in the measurement conditions can be detected by comparing the signal on the second electrode pair and on the fourth electrode pair.

6. The cassette module for a differential flowmeter according to claim 5, wherein the evaluation unit is configured so that a change in a position of the cassette module in the magnetic field can be detected by comparing the signal on the second electrode pair and the fourth electrode pair.

7. The cassette module for a differential flowmeter according to claim 5, wherein the second fluid-carrying channel includes a second channel first section and the second channel additional section,
   wherein the second channel additional section is a return section and
   wherein the second channel first section and the return section are arranged side by side with respect to a direction of the magnetic field.

8. The cassette module for a differential flowmeter according to claim 3, wherein the first fluid-carrying channel and the second fluid-carrying channel are arranged one after the other with respect to a direction of the magnetic field.

9. The cassette module for a differential flowmeter according to claim 3, wherein the first fluid-carrying channel has a first channel first section and a first channel return section, and wherein the first channel first section and the return section are arranged side by side with respect to the direction of the magnetic field.

10. The cassette module for a differential flowmeter according to claim 3, wherein the evaluation unit is adapted to initiate a recalibration in response to a finding of a change in the measurement conditions.

11. The cassette module for a differential flowmeter according to claim 10, wherein the evaluation unit is adapted to perform the recalibration in response to the finding of the change in the measurement conditions.

12. The cassette module for a differential flowmeter according to claim 11, having a short-circuit line and shut-off devices for short-circuiting the first fluid-carrying channel and the second fluid-carrying channel, and wherein for recalibration the shut-off devices can be controlled so that the first fluid-carrying channel and the second fluid-carrying channel are short-circuited.

13. The cassette module for a differential flowmeter according to claim 12, wherein a shut-off device is arranged in an inflow, in an outflow and in the short-circuit line.

14. The cassette module for a differential flowmeter according to claim 1, wherein the first channel additional section is a return section.

15. The cassette module for a differential flowmeter according to claim 2, wherein the second channel additional section is a return section.

* * * * *